United States Patent
Kuebelbeck et al.

(10) Patent No.: US 9,078,929 B2
(45) Date of Patent: Jul. 14, 2015

(54) ε-POLYLYSINE CONJUGATES AND THE USE THEREOF (75) Inventors: Armin Kuebelbeck, Bensheim (DE); Gregor Larbig, Gelnhausen (DE); Walter Mier, Bensheim (DE); Barbro Beijer, Nussloch (DE); Uwe Haberkorn, Schwetzingen (DE)

(73) Assignee: Merck Patent GmbH, Darmstadt (DE)

( * ) Notice: Subject to any disclaimer, the term of this patent is extended or adjusted under 35 U.S.C. 154(b) by 161 days.

(21) Appl. No.: 13/384,789

(22) PCT Filed: Jul. 9, 2010

(86) PCT No.: PCT/EP2010/004198
§ 371 (c)(1), (2), (4) Date: Jan. 19, 2012

(87) PCT Pub. No.: WO2011/009539
PCT Pub. Date: Jan. 27, 2011

(65) Prior Publication Data
US 2012/0122788 A1 May 17, 2012

(30) Foreign Application Priority Data
Jul. 20, 2009 (EP) .................... 09009393

(51) Int. Cl.
*A61K 38/00* (2006.01)
*A61P 13/12* (2006.01)
*C07K 5/00* (2006.01)
*C07K 7/00* (2006.01)
*C07K 16/00* (2006.01)
*C07K 17/00* (2006.01)
*A61K 38/04* (2006.01)
*A61K 47/48* (2006.01)
*A61K 49/08* (2006.01)
*A61K 51/04* (2006.01)
*C07K 7/06* (2006.01)
*C07K 14/00* (2006.01)
*C07K 7/08* (2006.01)

(52) U.S. Cl.
CPC ......... *A61K 47/48315* (2013.01); *A61K 49/085* (2013.01); *A61K 51/0497* (2013.01); *C07K 7/00* (2013.01); *C07K 7/06* (2013.01); *C07K 7/08* (2013.01); *C07K 14/00* (2013.01)

(58) Field of Classification Search
CPC ... A61K 47/48; A61K 47/48315; C07K 7/00; C07K 7/06; C07K 7/08; C07K 14/00
See application file for complete search history.

(56) References Cited

U.S. PATENT DOCUMENTS

2009/0209508 A1  8/2009  Lange et al.
2009/0287005 A1* 11/2009  Baker et al. .................. 549/510

FOREIGN PATENT DOCUMENTS

| WO | WO 90/13256 | * | 11/1990 |
| WO | WO 90/13256 A1 | | 11/1990 |
| WO | WO 03/086293 A2 | | 10/2003 |
| WO | WO 2007/023398 A2 | | 3/2007 |
| WO | WO 2008/017122 | * | 2/2008 |

OTHER PUBLICATIONS

Matsusaki et al, Self-assembling bionanoparticles of poly(epsilon-lysine) bearing cholesterol as a biomesogen, Biomacromolecules. Jul.-Aug. 2005;6(4):2374-9.*
Uzgiris et al, Conformation and structure of polymeric contrast agents for medical imaging, Biomacromolecules. Jan.-Feb. 2004;5(1):54-61.*
Steeghs et al, Small Molecule Tyrosine Kinase Inhibitors in the Treatment of Solid Tumors: An Update of Recent Developments, Ann Surg Oncol. Feb. 2007;14(2):942-53. Epub Nov. 14, 2006.*
Zahid et al, Identification of a Cardiac Specific Protein Transduction Domain by In Vivo Biopanning Using a M13 Phage Peptide Display Library in Mice, PLoS ONE, Aug. 2010, vol. 5, Issue 8, e12252).*
Szende et al, Antitumor effect of lysine-isopeptides, Cancer Cell International 2002, 2:4.*
International Search Report of PCT/EP2010/004198 (Sep. 3, 2010).
I.L. Shih et al., "Microbial Synthesis of Poly(e-lysine) and Its Various Applications", Bioresource Technology, vol. 97, No. 9 (2006) pp. 1148-1159.
D. Huang et al., "Design and Biophysical Characterization of Novel Polycationic e-Peptides for DNA Compaction and Delivery", Biomacromolecules, vol. 9, No. 1 (2008) pp. 321-330.
M. Matsusaki et al., "Self-Assembling Bionanoparticles of Poly(e-Lysine) Bearing Cholesterol as a Biomesogen", Biomacromolecules, vol. 6, No. 4 (2005) pp. 2374-2379.
M.V. Pimm et al., "In Labelling of a Branched Polypeptide Drug Carrier with a Poly(L-lysine) Backbone", International Journal of Pharmaceuticals, vol. 79, No. 1-3 (1992) pp. 77-80.
Kornguth, S.E. et al. "Preferential Binding of Radiolabeled Poly-L-lysines to C6 and U87 MG Glioblastomas Compared with Endothelial Cells in Vitro" Cancer Research, 49:6390-6395, Nov. 15, 1989.

* cited by examiner

*Primary Examiner* — Karheinz R Skowronek
*Assistant Examiner* — Sergio Coffa
(74) *Attorney, Agent, or Firm* — Millen, White, Zelano & Branigan, P.C.

(57) ABSTRACT

The present invention relates to ε-polylysine conjugates, in particular conjugates of ε-polylysine with compounds carrying carboxyl groups, and to the preparation and use thereof for targeting of the kidney.

17 Claims, 4 Drawing Sheets

DTPA

MAG3

DMSA

Fig. 4 eanalapril derivative 1 eanalapril derivative 2 eanalapril derivative 3 eanalapril derivative 4

ε-POLYLYSINE CONJUGATES AND THE USE THEREOF

The present invention relates to ε(epsilon)-polylysine conjugates, in particular conjugates of ε-polylysine with compounds carrying carboxyl groups, and to the preparation and use thereof for targeting of the kidney.

The kidney is an organ which is of importance, in particular, for the transport and excretion of various substances and in the production of hormones.

One function of the kidneys is the excretion of end products of metabolism, the so-called urophanic substances, and toxins from the body through the formation of urine, which is finally excreted from the body via the urinary tract. The kidney regulates the water balance and thus serves for long-term regulation of blood pressure. It regulates the electrolyte balance and the acid-base balance by control of the composition of urine. Furthermore, the kidney is an important organ for intermediary metabolism in the body (it effects gluconeogenesis). The kidney produces hormones, such as, for example, erythropoietin, for blood formation and is the site of degradation of peptide hormones. However, many functions of the kidney itself are also controlled by hormones.

The kidney is therefore an organ which is important to life, for which many diagnostic and therapeutic methods have already been developed. For example, immunosuppressants, cytostatics, immunotherapeutic agents, antiphlogistics, antibiotics, virostatics, antihypertensives, uricosurics, or diuretics are employed for the treatment of the kidney or for influencing kidney function. It is particularly important here that the medicaments reach the kidney in as targeted a manner as possible.

Equally, representation of the kidney in imaging methods is also of major importance.

With the aid of established nuclear-medical and radiological methods, such as SPECT, PET, ultrasound and MRT, enzymatic processes, metabolic processes, the expression of certain genes and molecular reactions, besides morphological structures, can be depicted by so-called molecular imaging. The imaging modalities mentioned above can, if necessary, be further supplemented by computer tomographic and optical imaging methods (near-infrared imaging, fluorescence tomography). The focus of "molecular imaging" is at present still on the diagnosis of cancer diseases, neurological questions and the monitoring of gene therapies, but in the future will be extended to all areas in which cellular changes have to be discovered as early as possible.

As signal source for the imaging methods, a "signal molecule" is generally coupled to a "carrier molecule". The "carrier molecule" ensures highly specific targeting by, for example, binding specifically to the target cells or becoming trapped therein. For example, the carrier molecule can be the ligand of a receptor or the substrate of an enzyme. The "signal molecule" can be rendered visible by means of one or more imaging techniques. Examples of signal molecules are, for example, complexing agents or chelating agents whose metal ions can be detected via imaging techniques. The compound or conjugate comprising signal molecule and carrier molecule is called the "diagnostic agent". The various imaging techniques will be discussed in detail below.

Computer Tomography (CT)

In classical radiography, the tissue-specific attenuation of X-rays is depicted on an X-ray film. "Hard tissues", for example bones, absorb a large amount of radiation here in contrast to "soft" tissue, such as fat and muscle. X-ray contrast agents used are substances which contain elements having a high atomic number, for example iodine-containing molecules for angiography. As a further development, radiography supplies cross-sectional images. In CT, radiographs are recorded from various directions by sensors (detectors) and reproduced by computer as three-dimensional radiography. Owing to the broad applicability of CT, this method is known as the "work-horse of classical radiology". However, the low sensitivity of the method limits its use as a method for molecular imaging.

Single Photon Emission Computed Tomography (SPECT)

Scintigraphy uses the gamma radiation of radioactively labelled substances (radiotracers) emitted by short-lived radionuclides. These accumulate specifically in the target tissue in the body. With the aid of a gamma camera, the emitted radiation is recorded and converted into an image. Single Photon Emission Computed Tomography (SPECT) is the three-dimensional variant of scintigraphy. In SPECT, the radiation is recorded from various angles as in CT, and a three-dimensional image is obtained in the computer. In static SPECT, the concentration of the radiotracer at a certain point in time is measured. In dynamic SPECT, the measurement is repeated at certain time intervals. In this way, the change in accumulation can be investigated.

Positron Emission Tomography (PET)

In clinical application, PET supplements the more structurally oriented imaging methods of diagnostic radiology. Positron emission tomography (PET) is a modern functionally imaging method. With the aid of positron-emitting atoms, it enables excellent resolution in the detection of radioisotopes (a resolution of 2-3 mm is achieved in modern PET instruments, even in the case of full-body tomographs). If these radioisotopes, for example $^{68}$Ga, are employed for the labelling of biomolecules, the biochemical processes in individual organs of the organism can be imaged. An essential advantage of nuclear-medical methods is the high sensitivity, owing to which the tracers can only be employed in tiny amounts (nanogram quantinties). Today, the PET camera is integrated with a CT instrument (this offers high local resolution of about <1 mm). PET/CT technology has introduced revolutionary results into diagnostics in recent years. The functional images of PET and the morphological information of CT in the same anatomical structures can thus be obtained in a single representation.

An organ which is very frequently and very intensively investigated in medical diagnostics is the kidney. The most frequent investigation method here is renal scintigraphy.

Renal Scintigraphy

Renal scintigraphy is a nuclear-medical investigation method which allows the assessment of renal function from static and dynamic points of view. The blood supply, function and excretion of each individual kidney are assessed here. It is an established method for the recognition of parenchymal scarring, in particular in children, and furthermore serves for the assessment of regional and side-separated renal function.

A distinction is made between two forms of renal scintigraphy:

Static Renal Scintigraphy

In static renal scintigraphy, the functional kidney tissue is represented using the radionuclide $^{99m}$Tc. The technetium here is bound in complex form to, for example, 2,3-dimercaptosuccinic acid (DMSA). Static renal scintigraphy is therefore principally suitable for the representation of kidneys having anomalies (dystrophy, horseshoe kidney, etc.) or state after inflammation.

Dynamic Renal Scintigraphy

By contrast, dynamic renal scintigraphy investigates renal function. Thus, the glomerular filtration rate, renal blood flow (RBF) and tubular secretion can be investigated with the question of renal function and clearance thereof.

Radiopharmaceuticals which are currently used are the following substances:
$^{99m}$Tc-MAG3 mercaptoacetyltriglycine
$^{99m}$Tc-DMSA 2,3-dimercaptosuccinic acid
$^{99m}$Tc-DTPA diethylenetriaminepentaacetic acid
$^{123}$I-OIH hippuran (ortho-iodohippuric acid)

Figure 3:
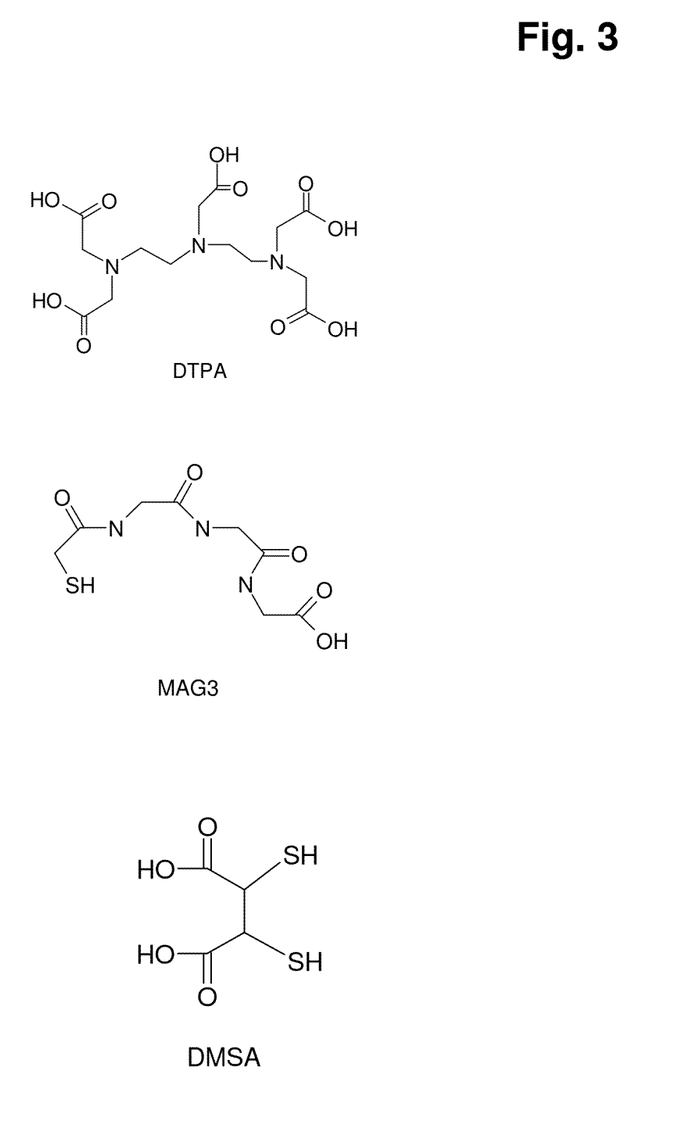
FIG. 3 shows the chemical structure of MAG3, DMSA and DTPA.

FIG. 3 shows the chemical structure of MAG3, DMSA and DTPA.

Renal function scintigraphy (=dynamic renal scintigraphy) is employed in the following indications:
for clarification of side-separated renal function in kidney diseases, such as, for example, kidney stones (nephrolithiasis), renal tumours, dystrophic (incorrectly located) kidneys or dysplastic (malformed) kidneys
for the investigation of part-function in the case of double kidneys
for the investigation of urinary flow disorders
for clarification of vesicorenal reflux (an anomaly of the urinary tract)
if renovascular hypertonia is suspected
for testing renal function before living kidney donation
for progress control of surgically repaired vascular constrictions or obstructions
for the assessment of transplanted kidneys
in emergency diagnosis if kidney injury (kidney trauma) is suspected
in the case of sudden greatly reduced urine excretion (anuria) in order to exclude a renal embolism or an acute urinary obstruction
in order to determine total clearance
in order to detect or exclude urine leakage To date, renal function scintigraphy has generally been carried out by means of SPECT, since the approved tracers MAG3 and DMSA can only be labelled with the SPECT nuclide $^{99m}$Tc. Consequently, it has to date not been possible to use the considerably improved possibilities today due to PET and PET/CT for renal function diagnosis.

It would also be desirable for therapeutic purposes if targeting of the kidney could be improved. Today, about 280 million people suffer from chronic kidney diseases. The use or dosage of medicaments for the treatment of kidney diseases is frequently restricted by side effects of the medicaments. If it were possible to develop a drug targeting concept, by means of which known or also new medicaments reach the kidney in a targeted manner, the therapeutic treatment of kidney diseases would be greatly improved.

WO 03/086293 describes an attempt to improve the flavour of medicaments by them forming a complex with polylysine or polyarginine. The complex here consists of an organic salt, i.e. there is no covalent bond, but instead an ionic bond, between polylysine/polyarginine and the medicament. Nothing is disclosed regarding the possibility of the use of polylysine conjugates in the drug targeting of the kidney.

Ing-Lung Shih et al., Bioresource Technology 97 (2006) 1148-1159, disclose the use of ε-polylysine in drug targeting. It is proposed that ε-polylysine be covalently bonded to active compounds. The aim of the approach described therein is an increase in the uptake rate in cells. Specificity for specific tissue is neither aimed at nor achieved.

The object of the present invention was therefore to provide a carrier or carrier molecule for a therapeutic agent or diagnostic agent which has the highest possible affinity and selectivity for the kidney.

Surprisingly, it has been found that conjugates of ε-polylysine or ε-polylysine derivatives with compounds carrying carboxyl groups have extremely high selectivity for the kidney. This means that these conjugates are taken up virtually exclusively by the kidney tissue. These conjugates, coupled to signal molecules, such as, for example, radioisotopes and/or active compounds, can be employed for the diagnostic and/or therapeutic treatment of the kidney.

The present invention therefore relates to a conjugate comprising at least one compound carrying carboxyl groups and a linear or branched oligomer which consists of peptidically linked monomer units and which is either built up in total from more than 50% (based on the number of monomer units) of ε-lysine monomer units or comprises at least 10 successive monomer units which are built up from at least 70% (based on the number of monomer units) of ε-lysine monomer units. Preference is given to the use of compounds carrying carboxyl groups in which the proportion of the carboxyl groups in the molar mass of the compound carrying carboxyl groups is greater than 30%, particularly preferably greater than 40%.

In a preferred embodiment, in particular for therapeutic applications, the conjugate additionally comprises at least one active compound, preferably covalently bonded.

In a preferred embodiment, the oligomer has a chain length of 10 to 50 monomer units.

In a particularly preferred embodiment, the oligomer consists only of ε-lysine monomer units, in particular only of ε-lysine units.

In a preferred embodiment, at least one compound carrying carboxyl groups is bonded via the amino group of an ε-lysine monomer unit, i.e. one or more ε-lysine monomer units carry on their amino group a compound carrying carboxyl groups which is conjugated directly or via a spacer.

In an embodiment, which is particularly preferred for diagnostic applications, the compound carrying carboxyl groups is a complexing agent, particularly preferably DOTA (=1,4,7,10-traazacyclododecane-N, -N', -N'', -N'''-tetraacetic acid) or DTPA (diethylenetriaminepentaacetic acid).

The present invention also relates to a process for the preparation of the compounds according to the invention which comprises at least the following process steps:
a) provision of an oligomer according to the invention which contains at least one reactive group,
b) conjugation of at least one optionally activated compound carrying carboxyl groups to the oligomer from step a)

In an embodiment of the process according to the invention, if the conjugate comprises a complexing agent, the compound obtained in step b) is brought into contact with metal salts in a further step c), so that metal ions are complexed by the complexing agents.

The present invention additionally relates to a conjugate according to the invention as medicament, such as, in particular, a therapeutic composition or an image-enhancing composition.

The present invention also relates to a medicament or pharmaceutical composition, in particular a therapeutic or image-enhancing composition, at least comprising a conjugate according to the invention.

The present invention also relates to a kit for the preparation of a medicament or pharmaceutical composition, in particular a therapeutic or image-enhancing composition, at least comprising a conjugate according to the invention. This conjugate can then be reacted, depending on the application, for example, with a suitable active compound for the preparation of a therapeutic composition or, if a complexing agent is present, with metal ions which have an image-enhancing and/or therapeutic action.

The present invention also relates to the use of the conjugate according to the invention for the preparation of macromolecule conjugates, where two or more conjugates according to the invention are bound to a macromolecule, and a macromolecule conjugate composed of at least two or more conjugates according to the invention which are covalently bonded to a macromolecule.

The present invention also relates to the use of a conjugate according to the invention for targeting of the kidney. The targeting of the kidney here preferably serves for enriching medicaments for pharmaceutical or diagnostic applications in the kidney, i.e. generating increased uptake in the kidney in relation to the remainder of the body.

Substances which improve the representation of the target organ in certain diagnostic methods act as image-enhancing composition or contrast medium or image-enhancing, generally by increasing the contrast to the environment or the signal of the target organ in relation to the environment.

A compound carrying carboxyl groups in accordance with the present invention is a chemical compound which contains at least one carboxyl group (—COOH) and at least one group or functionality for bonding to the oligomer of the conjugate according to the invention. The bonding to the oligomer can take place in any known manner which results in covalent bonding of the oligomer and compound carrying carboxyl groups. Examples of functional groups via which bonding can take place are —NH$_2$, —SH, —OH, -Hal (for example —Cl, —Br, —I), -alkyne, —NCS, —NCO, —SO$_2$Cl, -azide, -carbonate, -aldehyde, -epoxide, —COOH, —COOR, where R in this case is preferably a halogen or preferably an activator, i.e. a good leaving group, such as, for example, N-hydroxysuccinimide, pentafluorophenyl or para-nitrophenyl. An overview of possible covalent types of coupling is found, for example, in "Bioconjugate Techniques", Greg T. Hermanson, Academic Press, 1996, on pages 137 to 165.

The compound carrying carboxyl groups preferably contains two or more carboxyl groups. Examples of compounds carrying carboxyl groups which are suitable in accordance with the invention are: citric acid, succinic acid, fumaric acid, maleic acid, glutaric acid, adipic acid, tartaric acid, oxalic acid, malonic acid, succinic acid, glutaric acid, adipic acid, suberic acid, azelaic acid, sebacic acid, the corresponding branched fatty acids, maleic acid, fumaric acid, cyclohexanedicarboxylic acid and the corresponding position isomers and similar aliphatic dibasic acids; tetrahydrophthalic acid, 5-norbornene-2,3-dicarboxylic acid and similar alicyclic dibasic acids; tricarballytic acid, aconitic acid, trimesic acid and similar tribasic acids; adamantanetetracarboxylic acid, butanetetracarboxylic acid, cyclopentanetetracarboxylic acid, tetrahydrofurantetracarboxylic acid and similar tetrabasic acids; sugar acids, in particular aldaric acids, such as, for example, glucaric acid, galactaric acid; malic acid, tartaric acid, citric acid and similar hydroxy-fatty acids; trimellitic acid, pyromellitic acid, biphenyltetracarboxylic acid, benzophenonetetracarboxylic acid, diphenylsulfonetetracarboxylic acid and similar aromatic polycarboxylic acids.

In accordance with the invention, the compound carrying carboxyl groups can also be complexing agents which contain at least one carboxyl group, preferably two or more carboxyl groups, and at least one group or functionality for bonding to the oligomer of the conjugate according to the invention. Examples thereof are NOTA, TETA, EDTA or preferably DOTA or DTPA. In this case, the compounds carrying carboxyl groups simultaneously also fulfil the function of a complexing agent, which is particularly advantageous for diagnostic applications.

Preferred compounds carrying carboxyl groups are those which contain two or more free carboxyl groups after conjugation to the oligomer.

It has been found that the specificity achieved in the targeting of the kidney is particularly high if the carboxyl groups of the compound carrying carboxyl groups make up a large proportion of the molar mass of the compound carrying carboxyl groups. Preference is therefore given to compounds carrying carboxyl groups in which the proportion of the carboxyl groups in the molar mass is greater than 30%, preferably greater than 40%.

For example, the molar mass of DOTA is 404 g/mol. The 4 carboxyl groups thereof make up a proportion of 180 g/mol (4×COOH=4×45 g/mol). This gives a proportion of carboxyl groups in the molar mass of DOTA of about 44%.

Citric acid has a molar mass of 192 g/mol. The carboxyl groups (3×45 g/mol) make up 135 g/mol thereof. This gives a proportion of carboxyl groups in the molar mass of citric acid of about 70%.

Compounds carrying carboxyl groups which are particularly preferred in accordance with the invention are therefore those which contain two or more free carboxyl groups after conjugation to the oligomer and in which the proportion of the carboxyl groups in the molar mass is greater than 30%, preferably greater than 40%, such as, for example, DOTA, DTPA and citric acid.

A spacer, often also called a linker, effects a covalent bond between two parts of a molecule, in the present case, for example, between the oligomer according to the invention and a compound carrying carboxyl groups or an active compound. A spacer will generally be introduced if the connection between two moieties is not to take place only via a direct chemical bond, but instead a certain separation is to be generated between two moieties. Equally, a spacer can provide the chemical functionalities which are necessary in order to connect two parts of a molecule which would otherwise not react with one another. The conjugation of a spacer to the oligomer, the compound carrying carboxyl groups or an active compound preferably takes place via an amide or ester bond. Spacers can be, for example, aliphatic hydrocarbons, polyethers (such as polyethylene glycols), oligo-peptides or similar elements having a chain structure. The spacer may be stable, i.e. it cannot be cleaved under physiological conditions or can only be cleaved to a slight extent, or it may be unstable, i.e. it can be cleaved, at least under certain physiological conditions.

Active compounds, peptides, complexing agents or other functionalities can be bonded to the oligomer directly or by means of a spacer.

Examples of functional groups via which direct bonding can take place are —NH$_2$, —SH, —OH, -Hal (for example —Cl, —Br, —I), -alkyne, —NCS, —NCO, —SO$_2$Cl, -azide, -carbonate, -aldehyde, -epoxide, —COOH, —COOR, where R in this case is preferably a halogen or preferably an activator, i.e. a good leaving group, such as, for example, N-hydroxysuccinimide, pentafluorophenyl or para-nitrophenyl. An overview of possible covalent types of coupling is found, for example, in "Bioconjugate Techniques", Greg T. Hermanson, Academic Press, 1996, on pages 137 to 165.

For example, active compounds can be bonded to the conjugate according to the invention via a cleavable linker. This linker is then cleaved in vivo under certain conditions, for example by enzymatic or chemical cleavage, and liberates the active compound. Suitable for this purpose are linkers which contain carboxylate and disulfide bonds, in which the former groups are hydrolysed enzymatically or chemically and the latter are separated off by disulfide exchange, for example in the presence of glutathione.

An example of a cleavable spacer is also an oligopeptide which can be cleaved specifically with the aid of specific, endogenous or exogenous enzymes. Thus, for example, the peptide sequence DEVD (Asp-Glu-Val-Asp) is cleaved after apoptosis induction by Caspase-3. Thus, for example, an active compound or a compound carrying carboxyl groups which is bonded via a spacer of this type can be removed from the kidney after a certain residence time therein, or alternatively a corresponding functionality (presence or absence of a certain enzyme) of the kidney can also be checked. Further examples are the peptide sequences CPEN↓FFWGGGG or PENFF, which can be cleaved by matrix metalloprotease-13. A simple embodiment of a cleavable spacer is the formation of a carboxylate, which can easily be cleaved by esterases.

Alternatively, the spacer may contain an acid-labile structure, for example a hydrazone, an imine, a carboxyhydrazone, an acetal or ketal (see, for example, Haag-R, Kratz-F, Angewandte Chemie page 1218 (2006)).

In accordance with the invention, amino acids are compounds which carry at least one amino group and at least one carboxyl group. Examples are natural, proteinogenic amino acids or non-proteinogenic amino acids which occur in the organism or are prepared synthetically.

A peptide is a compound which is formed from the linking of two or more amino acids. The individual amino acids here are connected in a defined sequence to form a chain, usually unbranched. The amino acids in peptides and in the larger proteins are connected to one another via amide bonds.

In accordance with the invention, a solid phase is an organic, inorganic or organic/inorganic composite material which can be employed as resin or support in solid-phase synthesis. Furthermore, surfaces of mouldings, such as, for example, microtitre plates or particulate materials, such as, for example, organic or inorganic nanoparticles, metal particles or the like, are also regarded as solid phase in accordance with the invention.

In accordance with the invention, active compounds or active-compound molecules in accordance with the German Medicines Act are substances which are intended to be used as pharmaceutically active constituents in the preparation of medicaments or to become pharmaceutically active constituents on use in the preparation of medicaments (German Medicines Act §4 (19)). Active compounds generally cause a specific effect in an organism. An active compound according to the invention is typically a pharmaceutically active molecule or medicament, such as, for example, immunosuppressants, for example azathioprine, mycophenolate-mofetil, ciclosporin, tacrolimus, sirolimus, fingolimod or triptolide, cytostatics, for example bleomycin, dactinomycin, mitomycin, daunorubicin, doxorubicin, epirubicin, idarubicin, mitoxantron, doxofluridine, cisplatin, carboplatin, oxaliplatin, satraplatin, camptothecin, toptecan, irinotecan, amsacrine, etoposide, teniposide, cyclophosphamide, trofosfamide, melphalan, chlorambucil, estramustine, busulfan, chlorambucil, chlormethine, treosulfan, carmustine, lomustine, nimustine, procarbazine, streptozocine, dacarbazine, ifosfamide, temozolomide, thiotepa, vinorelbine, vincristine, vinblastine, vindesine, paclitaxel, docetaxel, methotrexate, pemetrexed, raltitrexed, fluorouracil, capecitabine, cytosinarabinoside, gemcitabine, tioguanine, pentostatin, mercaptopurine, fludarabine, caldribine, hydroxycarbamide, mitotane, azacitidine, cytarabine, nelarabine, bortezomib, anagrelide, in particular the protein kinase inhibitors, such as, for example, imatinib, erlotinib, sunitinib, sorafenib, dasatinib, lapatinib or nilotinib, immunotherapeutic agents, for example cetuximab, alemtuzumab and bevacizumab, antiphlogistics, for example naproxen, ibuprofen, indometacin, prednisolone, prednisone, hydrocortisone or budesonide, antibiotics, in particular the penicillins, such as, for example, benzylpenicillin, methicillin or amoxicillin, the cephalosporins, such as, for example, cefuroxim, cefotaxim, cefadroxil or cefixim, the β-lactamase inhibitors, such as, for example, clavulanic acid, sulbactam or tazobactam, the carbapenems, such as, for example, imipenem or meropenem, the monobactams, such as, for example, aztreonam, the tetracyclines, such as, for example, tetracycline, chlortetracycline, oxytetracycline, doxycycline, minocycline or tigecycline, the macrolide antibiotics, such as, for example, erythromycin A, the glycopeptide antibiotics, such as, for example, vancomycin, the enediynes, such as, for example, calicheamicin, virostatics, for example aciclovir, valaciclovir, ganciclovir, valganciclovir, penciclovir, famciclovir, brivudine, cidofovir, foscarnet, idoxuridine or tromantadine, antihypertensives, in particular the ACE inhibitors, such as, for example, benazepril, captopril, cilazapril, enalapril, fosinopril, lisinopril, perindopril, quinapril, ramipril, trandolapril or zofenopril, the sartans, such as, for example, losartan, balsartan, irbesartan, candesartan, eprosartan, olmesartan or telmisartan, the renin inhibitors, such as, for example, aliskiren, and the beta blockers, such as, for example, proproanolol, pindolol, sotalol, bopindolol, atenolol, bisorpolol, celiprolol, esmolol, metoprolol, nebivolol, oxprenolol, carvedilol or labetalol, uricosurics, for example probenecid or benzbromarone, or diuretics, for example acetazolamide, furosemide, torasemide, bumetanide, piretanide, azosemide, etacrynic acid, etozoline, hydrochlorothiazide, benzthiazide, chlorothiazide, chlorthalidone, indapamide, mefruside, metolazone, clopamide, xipamide, hydroflumethiazide, methyclothiazide, polythiazide, amiloride, triameterene, spironolactone, canrenone, eplerenone or spironolactone.

Further antitumour agents, for example agents which are effective against proliferating cells, are in accordance with the invention likewise active compounds. Illustrative antitumour agents include cytokines, such as, for example, interleukin-2 (IL-2), tumour necrosis factor or the like, lectin inflammation reaction promoters (selectins), such as, for example, L-selectin, E-selectin, P-selectin or the like, and similar molecules.

In accordance with the invention, one or more identical or different active-compound molecules can be bonded per conjugate according to the invention.

Equally, in particular in the case of macromolecules, such as, for example, relatively large active-compound molecules, for example proteins, it is conversely possible for two or more, preferably 2, 3, 4, 5, 6, 7, 8, 9 or 10, conjugates according to the invention to be bonded to one active-compound molecule in order to enable kidney-specific accumulation of the active compound. Covalent bonding of the conjugates according to the invention to the macromolecule typically also takes place here. In accordance with the invention, macromolecules are taken to be not only large molecules, such as proteins, but also any form of particles (for example nanoparticles), liposomes or other systems by means of which active compounds can be transported or to which active compounds can be bonded.

In addition to the active-compound molecules, or instead of the active-compound molecules, other functionalities, such as, for example, functionalities for diagnostic or imaging methods, may also be bonded to the conjugate according to the invention.

Equally, fluorine-containing side chains can be incorporated as functionality via optional spacers. The accumulation of the corresponding molecules in the kidneys can thus be represented with the aid of $^{19}F$ nuclear resonance tomography. Highly symmetrically arranged fluorine atoms, which have a uniform resonance frequency, are particularly advantageous here. In order to improve the $^{19}F$ signal, a contrast agent which is usual in nuclear spin tomography, such as, for example, gadobutrol (Magnevist®), can be used.

If the conjugate according to the invention comprises complexing agents, it is particularly advantageous to integrate gadolinium or manganese or another strongly paramagnetic metal ion which is known to the person skilled in the art with the aid of a complexing agent located on the conjugate according to the invention. Suitable complexing agents here are, for example, DOTA and DTPA.

Furthermore, complexing agents which do not belong to the group of compounds carrying carboxyl groups can be conjugated—also optionally via spacers. Examples are hydroxyquinoline, thiourea, guanidine, dithiocarbamate, hydroxamic acid, amide oxime, aminophosphoric acid, (cyclic) polyamino, mercapto, 1,3-dicarbonyl and crown ether radicals with various metals having in some cases very specific activities with respect to ions.

Functionalities for cell-specific targeting, such as, for example, antibodies, antibody fragments or aptamers, may also be bonded to the conjugate according to the invention. Fluorescent dyes or interleukins, such as IL-2, may also be bonded.

"Peptidically linked" in accordance with the invention means that an —NH—CO— bond is present between two monomer units, as is also present in peptides or proteins between two amino acids as monomer units. This means that two monomer units are linked in such a way that an —NH group of the one monomer is linked to a —C═O group of the other monomer. The following bonding structure accordingly arises: M-NH—CO-M-NH—CO-M-NH—CO-M, where M is the part of the monomer that is not involved in the bonding.

The conjugate of the present invention consists of at least two covalently bonded parts—a compound carrying carboxyl groups and an oligomer. In a preferred embodiment, the conjugate comprises an oligomer, one or more compounds carrying carboxyl groups and one or more active-compound molecules. In a particularly preferred embodiment, the conjugate according to the invention comprises a plurality of, i.e., for example, 2, 3, 4, 5, 6, 7, 8, 9 or 10, identical or different compounds carrying carboxyl groups and a plurality of, i.e., for example, 2, 3, 4, 5, 6, 7, 8, 9, or 10, identical or different active-compound molecules.

It has been found that the conjugates according to the invention accumulate particularly specifically in the kidney if a compound carrying carboxyl groups is covalently bonded to 10 to 80% of the monomer units.

In accordance with the invention, a complexing agent is any molecular structure which is capable of complexing metal ions, i.e. of forming a metalchelate complex with the metal ions. Complexing agents are frequently also known as chelating agents. Examples of complexing agents which are suitable in accordance with the invention are EDTA, NOTA, TETA, iminodiacetic acid, DOTA or DTPA. Particular preference is given in accordance with the invention to complexing agents which bind metal ions which can be detected in SPECT, PET, CT or MRT measurements. Preferred complexing agents are DOTA or DTPA or derivatives thereof. In accordance with the invention, complexing agents are both molecules to which the metal ions are already bonded and also molecules to which metal ions can be bonded, but are not bonded at the present stage.

Metal ions which are suitable in accordance with the invention for bonding to complexing agents are, for example, $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ and/or $Mn^{2+}$ or also the ions of radionuclides, such as gamma emitters, positron emitters, Auger electron emitters, alpha emitters and fluorescence emitters, for example $^{51}Cr$, $^{67}Ga$, $^{68}Ga$, $^{111}In$, $^{99m}Tc$, $^{140}La$, $^{175}Yb$, $^{153}Sm$, $^{166}Ho$, $^{88}Y$, $^{90}Y$, $^{149}Pm$, $^{177}Lu$, $^{47}Sc$, $^{142}Pr$, $^{159}Gd$, $^{212}Bi$, $^{72}As$, $^{72}Se$, $^{97}Ru$, $^{109}Pd$, $^{105}Rh$, $^{101m}Rh$, $^{119}Sb$, $^{128}Ba$, $^{197}Hg$, $^{211}At$, $^{169}Eu$, $^{203}Pb$, $^{212}Pb$, $^{64}Cu$, $^{67}Cu$, $^{188}Re$, $^{186}Re$, $^{198}Au$ and/or $^{199}Ag$.

Examples of suitable metal ions and their respective use are:

$^{111}In$ for SPECT $^{68}Ga$ for PET $^{90}Y$ for therapy

Gd, Eu, Mn for MRT tantalum, tungsten or other elements having a high atomic number for computer tomography

In accordance with the invention, the term oligomer is applied to the part of the conjugate that consists of an oligomer which consists of peptidically linked monomer units. The oligomer typically consists of 5 to 1000, preferably 8 to 100, particularly preferably 10 to 50, monomer units. In a particularly preferred embodiment, the oligomer consists of ε-polylysine which has between 8 and 100 monomer units, particularly preferably between 10 and 50 monomer units.

In other embodiments, however, up to 50% of the ε-lysine monomer units may be replaced by other monomer units and/or up to 50% of the ε-lysine monomer units may be derivatised or modified by the introduction of further functionalities. Likewise, the oligomer which consists of peptidically linked monomer units may comprise a plurality of successive monomer units which are not ε-lysine monomer units if it comprises at least 10 successive monomer units which consist of at least 70% (based on the number of monomer units), preferably at least 80%, of ε-lysine units. This is the case, for example, if a chain of 10 to 20 monomer units (for example comprising amino acids) in which no ε-lysine monomer unit is present and subsequently, for example, ten monomer units, of which eight are ε-lysine monomer units and two consist of other amino acids, is located at one end of the oligomer.

In accordance with the invention, the term monomer unit is applied to any part of the oligomer that is peptidically linked to at least one further part of the oligomer. Terminal monomer units here are generally only peptidically linked to one further monomer unit. Monomer units in the middle of the oligomer are peptidically linked to two further monomer units. Monomer units which are peptidically linked to three further monomers are located at branching points. In the case of monomer units in the middle of the oligomer, the monomer unit typically provides on the one hand the —NH part of the peptidic bond and on the other hand the —CO part.

In accordance with the invention, an ε-lysine monomer unit is an ε-lysine unit, an ornithine unit, a 2,3-diaminopropionic acid unit or a 2,4-diaminobutyric acid unit. The ε-lysine monomer unit preferably consists of an ε-lysine unit. The term unit here is in each case intended to show that it is a unit or monomer in a peptidically linked oligomer and not the free amino acid.

An ε-lysine unit has the following chemical structure:

The ε-lysine monomer units can be in the D or L form in the oligomer according to the invention.

Typical other monomer units which the oligomer according to the invention can comprise besides the ε-lysine monomer units are natural or synthetic amino acids, such as, in particular, alanine, ε-alanine, glycine, glutamic acid, aspartic acid or arginine.

Further typical monomer units are monomer units having a spacer function of the formula

I where SP can be a C1 to C20 alkylene, alkenylene or alkynylene group, in which one or more non-adjacent methylene groups may be replaced by —O—, —S—, —S(O)—, —SO$_2$—, —SO$_2$O—, —C(O)—, —C(O)O—, —CH$_2$—, —CHR'—, —CR'$_2$—, —CR'=CH—, —CH—CR'—, —CH=CH—, —CR'=CR'—, —C≡C—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=C$_1$— to C$_6$-alkyl, C$_3$- to C$_7$-cycloalkyl, unsubstituted or substituted phenyl.

SP preferably stands for linear C3 to C10-alkyl chains, linear C3-C10 chains having one or more alkylene groups, for ethylene glycol chains having two to ten ethylene glycol units or for oligopeptide chains.

Further typical monomer units are those which contain functionalities for the linking of spacers, active compounds, complexing agents, peptides, dyes, solubilisers, protecting groups, a solid phase or similar components or to which components such as active compounds, complexing agents, peptides, solubilisers, protecting groups, a solid phase or dyes are already bonded directly or via a spacer. Monomer units of this type preferably have at least one of the following functional groups —NH$_2$, —SH, —OH, -Hal (for example —Cl, —Br, —I), -alkyne, —NCS, —NCO, —SO$_2$Cl, -azide, -carbonate, -aldehyde, -epoxide, —COOH, —COOR, where R in this case is preferably a halogen or preferably an activator, i.e. a good leaving group, such as, for example, N-hydroxysuccinimide, pentafluorophenyl or para-nitrophenyl, or are linked to active compounds, complexing agents, peptides, dyes or similar components via a functional group of this type.

Furthermore, the oligomer according to the invention may comprise ε-lysine monomer units which are derivatised. These are monomer units in which further functionalities (F1/F2) are correspondingly bonded to the NH group and/or the amino group. F1 and F2 here can be, independently of one another, an acetyl group or also active compounds, complexing agents, peptides, dyes, solubilisers, protecting groups, a solid phase or similar components bonded directly or via a spacer. A corresponding ε-lysine unit in which a derivatisation has been introduced with the groups F1 and/or F2 is depicted in formula II.

II

It is evident to the person skilled in the art that the formulae depicted above depict monomer units in the middle of the oligomer chain and that terminal monomer units, depending on whether they are located at the C- or N-terminal end, in each case carry a COOH or COOR group instead of —CO— or carry an NH$_2$, NF1H, NF1R, NHR or NR$_2$ group instead of —NH— or —NF1-, where R is typically H, linear or branched C1-C6 alkyl, a spacer function for the bonding of active compounds, complexing agents, peptides, dyes, solubilisers, protecting groups, a solid phase or similar components, or an active compound, complexing agent, peptide, dye, solubiliser, protecting group, a solid phase or similar component bonded directly or via a spacer.

Accordingly, ε-polylysine derivatives are oligomers according to the invention which are not built up entirely from ε-lysine units, but instead in which other ε-lysine monomer units, such as, for example, ornithine units, occur and/or in which, in accordance with the specifications according to the invention, some of the monomer units are built up, for example, from other amino acids than ε-lysine, ornithine, 2,3-diaminopropionic acid or 2,4-diaminobutyric acid and/or from compounds of the formula I.

The present invention is based on the surprising effect that conjugates of ε-polylysine and ε-polylysine derivatives with compounds carrying carboxyl groups accumulate virtually exclusively in the kidney, for example after injection into the bloodstream or after subcutaneous injection. Correspondingly, the conjugates according to the invention are suitable for use in therapeutic methods for the treatment of the kidney, in imaging methods for the representation of the kidney and for kidney targeting.

The compounds according to the invention are preferably prepared starting from ε-polylysine by conjugating the corresponding compounds carrying carboxyl groups and preferably one or more active-compound molecules or further functionalities, optionally after corresponding activation.

ε-Polylysine is a homopolymer of the amino acid L-lysine. ε-Polylysine is produced by the bacterium *Streptomyces albulus* in an aerobic process. This naturally produced ε-polylysine comprises approximately 30 L-lysine units. ε-Polylysine is approved in Japan as antimicrobial preservative for foods. In contrast to α-polylysine, ε-polylysine is not enzymatically degraded by proteases.

Any type of ε-polylysine can be employed in accordance with the invention, i.e., for example, ε-polylysine produced naturally, produced by genetic engineering or produced synthetically. The chemical synthesis of ε-polylysine is carried out, in a corresponding manner to the conventional peptide synthesis, using correspondingly protected L-lysine, so that the peptide bonding takes place via the ε-amino group of the side chain.

For the preparation of the compounds according to the invention, ε-polylysine having a certain chain length can be employed (for example synthetically produced ε-polylysine or purified natural ε-polylysine) or also a mixture of ε-polylysine of various chain length, as obtained, for example, naturally from *Streptomyces albulus*. In accordance with the invention, both ε-polylysine having a certain chain length and also mixtures of ε-polylysine of various chain length or mixtures comprising various ε-polylysine derivatives therefore fall under the term ε-polylysine and ε-polylysine derivatives.

It has furthermore been found that not only conjugates of ε-polylysine, but also conjugates of ε-polylysine derivatives, exhibit excellent accumulation in the kidney.

Typical conjugates which are suitable in accordance with the invention can also be represented by formula III $$A\text{-}(Lys)_n\text{-}E \qquad\qquad III$$

in which
n is a number between 5 and 1000,
A is
  one or more charged or uncharged end groups bonded directly or via a spacer or a dendritic functionality, for example hydrogen, —CN, —OR', —NR'$_2$, —P(O)R'$_2$, —P(O)(OR')$_2$, —P(O)(NR'$_2$)$_2$, —C(O)R', —C(O)OR', —C(O)OH, —C(O)NR'$_2$, —SO$_2$NR'$_2$, —C(O)Hal, SO$_2$OH, —SO$_2$Hal, —NO$_2$, -Hal or
  one or more groups bonded directly or via a spacer or a dendritic functionality, such as, for example, compounds carrying carboxyl groups, active-compound molecules, complexing agents, dyes, one or more identical or different amino acids, peptides, proteins, solubilisers, protecting groups or a solid phase
E is
  one or more charged or uncharged end groups bonded directly or via a spacer or a dendritic functionality, for example hydrogen, —CN, —OR', —NH$_2$, NHR', —NR'$_2$, —P(O)R'$_2$, —P(O)(OR')$_2$, —P(O)(NR'$_2$)$_2$, —C(O)R', —C(O)OR', —C(O)OH, —C(O)NR'$_2$, —SO$_2$NR'$_2$, —C(O)Hal, SO$_2$OH, —SO$_2$Hal, —NO$_2$, -Hal or
one or more groups bonded directly or via a spacer or a dendritic functionality, such as, for example, compounds carrying carboxyl groups, active-compound molecules, complexing agents, dyes, one or more identical or different amino acids, peptides, proteins, solubilisers, protecting groups or a solid phase,
Lys is, independently of one another,
  an ε-lysine monomer unit corresponding to the definition already given
  a monomer unit conforming to formula I or II
  a group conforming to formula IV $$(NH\text{-}M\text{-}CO) \qquad\qquad IV$$

where M can denote, independently of one another,
  —O—, —S—, —S(O)—, —SO$_2$—, —SO$_2$O—, —C(O)—, —C(O)O—, —CH$_2$—, —CHR'—, —CR'$_2$—, —CR'=CH—, —CH—CR'—, —CH=CH—, —CR'=CR'—, —C≡C—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— or
  straight-chain or branched alkyl having 1 to 20 C atoms,
  straight-chain or branched alkenyl having 2-20 C atoms and one or more double bonds,
  straight-chain or branched alkynyl having 2-20 C atoms and one or more triple bonds,
  saturated, partially or fully unsaturated cycloalkyl having 3-7 C atoms, which may be substituted by alkyl groups having 1-6 C atoms,
where one or more non-adjacent methylene groups may be replaced by —O— or —S— and adjacent methylene groups may be replaced by alkenyl or alkynyl groups,
where one or more methylene groups may be replaced, independently of one another, by —O—, —S—, —S(O)—, —SO$_2$—, —SO$_2$O—, —C(O)—, —C(O)O—, —CH$_2$—, —CHR'—, —CR'$_2$—, —CR'=CH—, —CH—CR'—, —CH=CH—, —CR'=CR'—, —C≡C—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—
and one or more methylene groups present in M may be mono- or disubstituted, independently of one another, by R", where
R' is linear or branched C$_1$- to C$_8$-alkyl, C$_3$- to C$_7$-cycloalkyl, unsubstituted or substituted phenyl and
R" is linear or branched C$_1$- to C$_8$-alkyl, C$_3$- to C$_7$-cycloalkyl, unsubstituted or substituted phenyl
or —CN, —OR', —NH$_2$, NHR', —NR'$_2$, —P(O)R'$_2$, —P(O)(OR')$_2$, —P(O)(NR'$_2$)$_2$, —C(O)R', —O(O)OR', —O(O)OH, —C(O)NR'$_2$, —SO$_2$NR'$_2$, —C(O)Hal, SO$_2$OH, —SO$_2$Hal, —NO$_2$, -Hal and
Hal=—F, —Cl, —Br or —I,
where compounds carrying carboxyl groups, active compounds, complexing agents, peptides, solubilisers, protecting groups, a solid phase, dyes or similar components may be bonded, directly or via a spacer, to all functional groups which are suitable for conjugation (for example NH, NH$_2$, COOH, OH, —SH, -Hal (for example —Cl, —Br, —I), -alkyne, -azide, -aldehyde) of the monomer units Lys, independently of one another, with the proviso that the compound according to the invention contains at least one compound carrying carboxyl groups and either more than 50% of the monomer units (based on the number of monomer units) are ε-lysine monomer units or at least 70% (based on the number of monomer units) of at least 10 successive monomer units are ε-lysine monomer units.

In a preferred embodiment of the compound according to the invention, A is —C(O)OR', —C(O)OH, —C(O)NR'$_2$ or —C(O)Hal or one or more components bonded directly or via a spacer or a dendritic functionality, such as compounds carrying carboxyl groups, active compounds, complexing agents, peptides, solubilisers, protecting groups, a solid phase or dyes.

A is particularly preferably —OH, —OCH$_3$, —OCH$_2$CH$_3$ or one or more active-compound molecules bonded directly or via a spacer or a dendritic functionality.

In a preferred embodiment, E is
—H, —CH$_3$, —CH$_2$CH$_3$ or
or
one or more components bonded directly or via a spacer or a dendritic functionality, such as compounds carrying carboxyl groups, active compounds, complexing agents, peptides, solubilisers, protecting groups, a solid phase or dyes. E is particularly preferably
one or more active-compound molecules bonded directly or via a spacer or
a dendritic functionality.

If the compound according to the invention contains one or more groups Lys which contain an NH$_2$ or COOH group, further monomer units may be bonded via them via a peptidic bond, and singly or multiply branched compounds arise. The compounds according to the invention are preferably unbranched.

n is preferably a number between 8 and 100, particularly preferably between 10 and 50.

The conjugates according to the invention preferably comprise not only one, but instead a plurality of compounds carrying carboxyl groups. These can be bonded directly or via a spacer to the carboxyl- and/or amino-terminal end of the oligomer and/or to functional group of the monomer units which is suitable for conjugation (for example NH, —NH$_2$, —COOH, —OH, —SH, -Hal (for example —Cl, —Br, —I), -alkyne, -azide, -aldehyde).

In a preferred embodiment, the bonding of the compounds carrying carboxyl groups takes place via amino groups of the monomer units, for example the free amino group of ε-lysine.

The conjugate according to the invention should preferably contain at least one compound carrying carboxyl groups per 10 monomer units, particularly preferably between 3 and 6 compounds carrying carboxyl groups per 10 monomer units. Equally, however, it is also possible for one compound carrying carboxyl groups to be bonded to more than 9 of 10 monomer units or to all monomer units. The optimum number of compounds carrying carboxyl groups per 10 monomer units depends on the type of the compound carrying carboxyl groups and the type of the monomer units. The above-mentioned preferred number of compounds carrying carboxyl groups per monomer unit apply, in particular, to oligomers which are built up entirely from ε-lysine monomer units. The distribution of the compounds carrying carboxyl groups in the conjugate according to the invention can be random, meaning that, for example, the first monomer units contain —NH$_2$, followed by a monomer unit with a compound carrying carboxyl groups, then again one containing —NH$_2$, then two times a monomer unit which carries a compound carrying carboxyl groups, then again twice one containing —NH$_2$, etc.

Equally, the distribution of the complexing agents in the compound according to the invention may also be ordered in such a way that, for example, each second monomer unit has a compound carrying carboxyl groups bonded thereto. The ordering may also take place in such a way that all monomer units at one end of the conjugate according to the invention have a conjugated compound carrying carboxyl groups, while the remainder of the monomers contain free NH$_2$ functions.

The compounds carrying carboxyl groups are preferably randomly distributed in the conjugates according to the invention.

The conjugates according to the invention can be prepared, in particular, by various processes known to the person skilled in the art in the area of peptide synthesis.

1. Synthesis Starting from ε-polylysine

Here, synthetic or natural ε-polylysine of uniform or various chain length is typically reacted with the corresponding compounds carrying carboxyl groups in solution. To this end, for example, firstly the compounds carrying carboxyl groups can be activated. This can be carried out, for example, by activation of one or more of their carboxyl groups by converting them into the active ester or acid chloride. This is followed by the reaction with ε-polylysine, where the conjugation preferably takes place at the free amino groups. Alternatively, for example, one or more carboxyl groups of the compound carrying carboxyl groups can be activated using a coupling reagent, such as dicyclohexylcarbodiimide or HATU, and reacted with the ε-polylysine, where the conjugation preferably takes place at the free amino groups. Reaction conditions for reactions of this type are known to the person skilled in the art. Suitable solvents are, for example, water, acetonitrile, DMSO, DMF, dioxane, THF, methanol or mixtures of two or more of the said solvents.

2. Solid-Phase Synthesis

In particular if the conjugate is to comprise one or more monomer units which do not consist of ε-lysine or which consist of derivatised ε-lysine monomer units, a solid-phase synthesis for the preparation of the conjugates according to the invention may be advantageous. This solid-phase synthesis is carried out in a corresponding manner to a conventional peptide synthesis (for example Fmoc peptide synthesis or Boc peptide synthesis). Solid-phase syntheses of this type are known to the person skilled in the art. Suitable textbooks for peptide synthesis are Solid-Phase Peptide Synthesis: 289 (Methods in Enzymology) by Sidney P. Colowick (author), Gregg B. Fields (publisher), Melvin I. Simon (publisher) Academic Press Inc (November 1997) or Fmoc Solid Phase Peptide Synthesis: A Practical Approach by W. Chan (author), W. C. Chan (publisher), Peter D. White (publisher) "Oxford Univ Pr (2 Mar. 2000). The monomers employed in each case are selected here in such a way that an oligomer or conjugate corresponding to the present invention is formed. Depending on the type of monomer unit, the synthesis can be carried out using a derivatised monomer unit directly or a monomer unit which is firstly protected at the site intended for the derivatisation. When the synthesis of the oligomer is complete, the final derivatisation with the compounds carrying carboxyl groups, active compounds, etc., can then be carried out either on the solid phase or after cleaving-off from the solid phase in solution.

The bonding of the compounds carrying carboxyl groups in this case preferably takes place to the finished oligomer, i.e. either still on the solid phase when the solid-phase synthesis of the oligomer is complete or after the latter has been cleaved off in solution.

If the compound carrying carboxyl groups or an active compound or similar components (the process is described below by way of example for a complexing agent) is to be bonded, for example, to the N-terminal end of the oligomer, the oligomers are typically generated with an amino-terminal protecting group, such as, for example, Fmoc. If the complexing agent is able to withstand the conditions used for cleaving off the oligomer from the synthesis resin and for deprotecting the side chains, the Fmoc can be cleaved off from the N terminal of the complete resin-bound polypeptide, enabling the complexing agent to be bonded to the free N-terminal amine. In such cases, the complexing agent is typically activated by processes which are generally known in the art for producing an active ester or active carbonate group which is effective for forming an amide or carbamate bond to the oligomer amino group. It is of course also possible to use a different linking chemistry.

In order to help to minimise side reactions here, guanidino and amidino groups may be blocked using conventional protecting groups, such as, for example, carbobenzyloxy groups (CBZ), di-t-BOC, PMC, Pbf, N—NO$_2$ and the like.

Coupling reactions are carried out by known coupling processes in solvents, such as, for example, N,N-dimethylformamide (DMF), N-methyl-pyrrolidone, dichloromethane and/or water. Illustrative coupling reagents include O-benzotriazolyloxytetramethyluronium hexafluorophosphate (HATU), dicyclohexylcarbodiimide, bromo-tris(pyrrolidino)phosphonium bromide (PyBroP), etc. Other reagents may be present, such as, for example, N,N-dimethylaminopyridine (DMAP), 4-pyrrolidinopyridine, N-hydroxysuccinimide or N-hydroxybenzotriazole.

Correspondingly, the bonding of compounds carrying carboxyl groups, active compounds, complexing agents or similar components can also take place to the amino groups of the non-terminal ε-lysine monomer units.

If the molecule contains complexing agents, the metal ions can be complexed by known methods.

The present invention additionally relates to the use of the conjugates according to the invention for the preparation of a pharmaceutical composition or a medicament, in particular a therapeutic composition, and/or an image-enhancing composition (for example a contrast agent) and/or a radiolabelled tracer for nuclear-medical imaging.

The present invention additionally relates to the conjugates according to the invention to which one or more active compounds are preferably covalently bonded, and/or pharmaceutically usable salts and stereoisomers thereof, including mixtures thereof in all ratios, and optionally excipients and/or adjuvants
- as medicament
- for use as medicament
- as active compound or active component in a medicament
- as diagnostic agent
- for use as diagnostic agent
- for use in the targeting of the kidney
- and, in particular, as medicament for the treatment of diseases of the kidney.

A therapeutic composition generally consists at least of the active compound—in this case the conjugate according to the invention with active compound preferably covalently bonded—and one or more suitable solvents and/or excipients which allow application of the therapeutic composition.

A diagnostic composition or diagnostic agent serves as image-enhancing or imaging composition in diagnostic methods. A diagnostic agent generally consists at least of the signal source, i.e. the imaging and/or image-enhancing component—in this case the conjugate according to the invention, where in this case at least one compound carrying carboxyl groups in the conjugate is preferably a complexing agent—and one or more suitable solvents and/or excipients which allow application of the diagnostic composition.

For diagnostic applications, the conjugate according to the invention preferably serves as signal source in an image-enhancing contrast medium, enabling the latter to be detected by means of nuclear-medical and/or radiological methods, such as SPECT, PET, ultrasound, and or also by magnetic resonance tomography, computer-tomographic and optical imaging methods (near-infrared imaging). Detection methods and applications of image-enhancing contrast media are known to the person skilled in the art. Examples of suitable applications are the diagnosis of cancer diseases, neurological questions, checking the response to a therapy, checking of the degree of damage of a kidney in the case of, for example, autoimmune diseases, and monitoring of gene therapies, but also the recognition of cellular changes.

The invention furthermore relates to medicaments or pharmaceutical compositions comprising at least one conjugate according to the invention and/or pharmaceutically usable salts and stereoisomers thereof, including mixtures thereof in all ratios, and optionally excipients and/or adjuvants.

Pharmaceutical compositions or medicaments can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or β-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The conjugates according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The conjugates according to the invention can also be delivered using monoclonal antibodies as individual carriers to which the conjugates are coupled. The conjugates can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-$\epsilon$-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

The conjugates according to the invention are preferably administered parenterally.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of the conjugate according to the invention depends on a number of factors, including the type of coupled active compound, the age and weight of the patient, the precise condition that requires treatment, and its severity, the nature of the formulation and the method of administration.

The present invention also relates to a kit for the preparation of a pharmaceutical composition, in particular an image-enhancing or therapeutic composition, at least comprising a conjugate according to the invention. If this conjugate contains a complexing agent, this has preferably still not complexed any metal ions having an image-enhancing or therapeutic action.

The conjugate according to the invention can be in dissolved form in the kit in a solvent (for example an aqueous buffer) or preferably in the form of the lyophilisate.

Since the metal ions that are complexed by the complexing agent of the conjugate according to the invention are radioactive for many applications, pharmaceutical compositions which comprise the conjugate cannot be prepared as far in advance as desired. Furthermore, owing to the radioactivity, certain procedures regarding occupational safety must be followed during the preparation. For this reason, it is preferred in accordance with the invention to provide a kit which comprises the conjugate according to the invention, where the complexing agent has not yet complexed the metal ions necessary for the final application.

It has been found that the conjugates according to the invention have already accumulated specifically, i.e. exclusively or virtually exclusively, in the kidney a short time after application. In the case of the preferred intravenous administration of the conjugates according to the invention, accumulation in the kidney is observed after only 5 minutes. After one hour, more than 30%, preferably more than 50%, particularly preferably more than 70%, very particularly preferably more than 80%, of the injected dose is located in the kidney (% data based on measurement of the radioactivity).

In organ distribution studies with radiolabelled conjugates according to the invention (for example PET measurements or non-invasive imaging), the conjugates according to the invention typically exhibit at least a two-fold, preferably at least a five-fold, particularly preferably at least a ten-fold enrichment in the kidney in relation to the remainder of the body (blood, heart, lung, spleen, liver, muscle, brain) one hour after application. This means that the signal, which correlates directly with the amount of radiolabelled compound, in the kidney is at least twice as strong as the sum of the signals obtained from blood, heart, lung, spleen, liver, muscle and brain together.

The conjugates according to the invention can therefore be employed extremely well for diagnostic applications, such as renal scintigraphy, renal PET and renal MRT, functional testing of the kidney in general, for the therapy and diagnosis of renal cancer and, if desired, metastases of renal cancer, CT of the kidney and/or ultrasound of the kidney.

The therapeutic application is, in particular, in the drug targeting for the organ the kidney. In particular, the conjugates according to the invention can serve as medicaments for the treatment of diseases of the kidney or of diseases in the treatment of which medicaments are employed whose site of action is the kidney. One or more active compounds, such as antibiotics, inflammation inhibitors, ACE inhibitors, diuretics, immunosuppressants or chemotherapeutic agents, are preferably bonded to the conjugates according to the invention, for example via cleavable spacer sequences.

The use of the conjugates according to the invention for blocking the resorption of kidney-toxic substances is also possible.

In accordance with the invention, targeting of the kidney means the achievement of increased uptake of the applied substance in the kidney in relation to the remainder of the body. During targeting of the kidney with the conjugate according to the invention, at least a two-fold, preferably at least a five-fold, particularly preferably at least a ten-fold enrichment is preferably achieved in the kidney in relation to the remainder of the body (blood, heart, lung, spleen, liver, muscle, brain) by administration of a conjugate according to the invention. These values are determined by means of organ distribution studies with radiolabelled conjugates according to the invention (for example PET measurements or non-invasive imaging). The enrichment in the kidney typically takes place after 30 minutes to 8 hours, depending on the type of application.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding application EP 09009393.1-20, filed on 20 Jul. 2009, is incorporated into this application by way of reference.

EXAMPLES

1. Material Syntheses

Example 1

ε-L-polylysine-DOTA

DOTA 2,6-difluorophenyl ester: From DOTA and 2,6-difluorophenol with DCC (Mier et al. Bioconjugate Chem. 2005, 16, 237)

ε-L-Polylysine, average molar mass about 4000 (principally consisting of 29-34 lysine units), is purchased as 25% aqueous solution from Chisso Corp. (Japan) and lyophilised. ε-Polylysine (30 mg) is dissolved in water (2000), and a solution of DOTA 2,6-difluorophenyl ester (100 mg) in methanol (1 ml) is added, and 100 µl of N,N-diisopropylethylamine are added, and the mixture is stirred at RT for 2 days. DOTA 2,6-difluorophenyl ester (100 mg) was then again added, and the mixture was stirred overnight at RT. The mixture is then diluted with water and purified preparatively by HPLC. Clean fractions are lyophilised together. DOTA-ε-polylysine (98 mg) is obtained as colourless solid substance. The number of DOTA units per molecule of ε-polylysine is determined by loading with Gd and by MS as being about 10 DOTA units per molecule of ε-polylysine; i.e. about 30% of the amino groups of the ε-polylysine have reacted.

Figure 1:
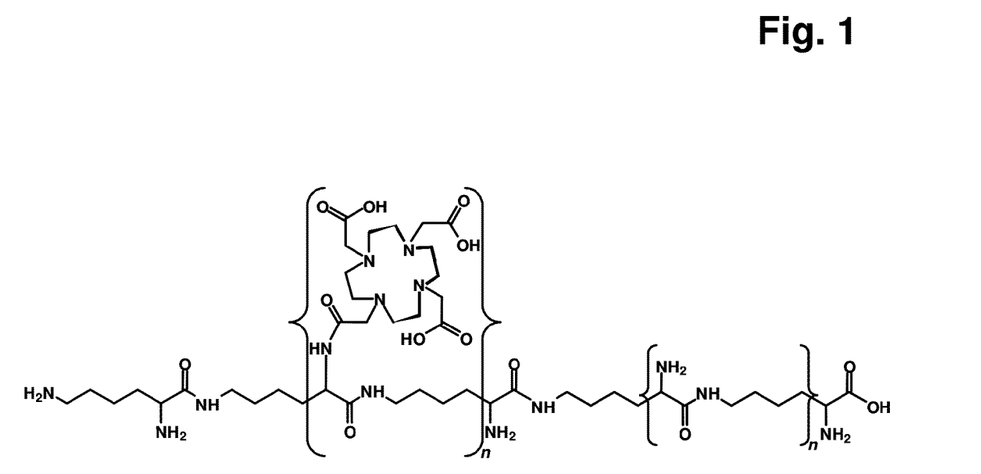
FIG. 1 shows a diagrammatic representation of the compound according to the invention obtained in Synthesis Example 1.
Figure 2:
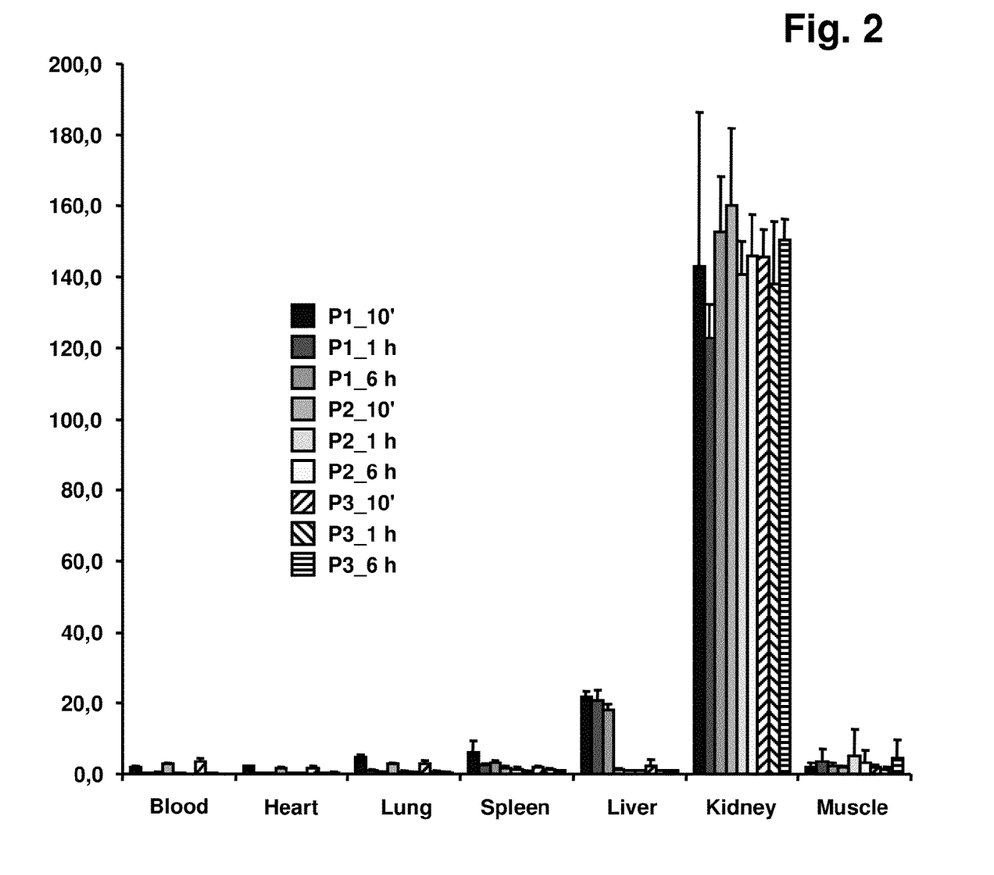
FIG. 2 shows the organ distribution of $^{111}$In-loaded ε-polylysine-DOTA. Further details are given in Use Example 1.

FIG. 2 shows a diagrammatic representation of the compound obtained in Example 1, where the DOTA modifications, in contrast to the simplified representation in FIG. 2, are of course randomly distributed in the molecule.

Example 2

ε-L-polylysine-DTPA 75 mg of ε-L-polylysine and 310 mg of DTPA difluorophenyl ester tetra-t-butyl ester are dissolved in 4 ml of methanol and stirred at RT for 20 h. The reaction solution is evaporated, and 4 ml of TFA+100 µl of water are added to the residue and left to stand for 20 h. The product is precipitated using diethyl ether. Purification by HPLC and lyophilisation gives 150 mg as colourless solid.

Example 3

Loading with $^{111}$In 1.5 mg of ε-L-polylysine-DOTA are dissolved in 500 µl of ethanol, 100 µl of DMSO and 500 µl of 0.4 M sodium acetate buffer, pH 5. 30 µl of this solution are diluted with 30 µl of buffer, $^{111}$InCl$_3$ (20 MBq) is added, and the mixture is heated at 70° C. for 8 min. Radio-HPLC shows complete complexing.

1.2 mg of ε-L-polylysine-DTPA are dissolved in 400 µl of 0.4 M sodium acetate buffer, pH 5. 20 MBq of $^{111}$InCl$_3$ are added to 80 µl of this solution, and the mixture is heated at 70° C. for 10 min. Radio-HPLC shows complete complexing.

Example 4

Loading with $^{68}$Ga

50 µl of the solution of ε-L-polylysine-DOTA from Example 3 are added to 100 µl of a solution of 50 MBq of $^{68}$GaCl$_3$ (pH 3), and the mixture is heated at 95° C. for 10 min. HPLC shows complete complexing.

Example 5

Loading with Gd 10 mg of ε-L-polylysine-DOTA and 50 mg of GdCl$_3$ hexahydrate are heated at 60° C. for 30 min in 600 µl of 0.4 M sodium acetate buffer pH 5. Purification by HPLC and lyophilisation gives 10 mg as colourless solid.

Example 6

EPL-DOTA Modification Using $^{19}$F 50 mg of ε-L-polylysine-DOTA are dissolved in 3 ml of methanol, and 200 µl of triethylamine and 200 µl of ethyl trifluoroacetate are added, and the mixture is stirred at RT for 1 h. Purification by RP-HPLC using an elution gradient comprising water and acetonitrile and lyophilisation gives 35 mg as colourless solid.

Example 7

Enalapril Derivative of ε-polylysine

Enalapril: Enalapril maleate (Bosche Scientific) is applied to a column containing Dowex 50 W×8 and washed with water until neutral. Enalapril is then eluted with 2% pyridine in water, the solvents are evaporated, and the residue is evaporated a number of times with acetonitrile. Enalapril is obtained as colourless oil and is used further directly.

Enalapril t-butyl ester: Synthesis is carried out from enalapril and N,N'-dicyclohexyl-O-t-butylisourea (Chadran, Ravi US 2006241017)

Enalaprilate t-butyl ester: Synthesis is carried out from enalapril t-butyl ester using NaOH (Iwasaki et al. Chem. Pharm. Bull. 37(2) 280 (1989)

N,N'-Diisopropyl-O-benzylisourea: Synthesis is carried out from benzyl alcohol and N,N'-dicyclohexylcarbodiimide (Mathias, Synthesis 1979, 561.)

Benzyl 6-hydroxyhexanoate: A solution of N,N'-diisopropyl-abenzyliso-urea (2.34 g; 10 mmol) in THF (8 ml) is added to 6-hydroxyhexanoic acid (ABCR) (1.32 g; 10 mmol), and the mixture is stirred at RT for 2 days. The solid material is filtered off, and the filtrate is evaporated. The residue is eluted on silica gel with ethyl acetate:hexane 1:2 to 1:1. Yield 90%.

Benzyl hexanoate 6-O—N,N'-diisopropylisourea: N,N'-Diisopropylcarbodiimide (1.14 g, 9 mmol) is added to benzyl 6-hydroxyhexanoate (2.0 g; 9 mmol), CuCl (30 mg) and THF (6 ml) are added, and the mixture is stirred overnight at RT. The mixture is then diluted with THF and filtered through neutral aluminium oxide in a frit and rinsed with THF. The filtrate is evaporated, the residue is taken up in diethyl ether, the solid material is filtered off, and the filtrate is evaporated. The product is used without further purification.

Figure 4:
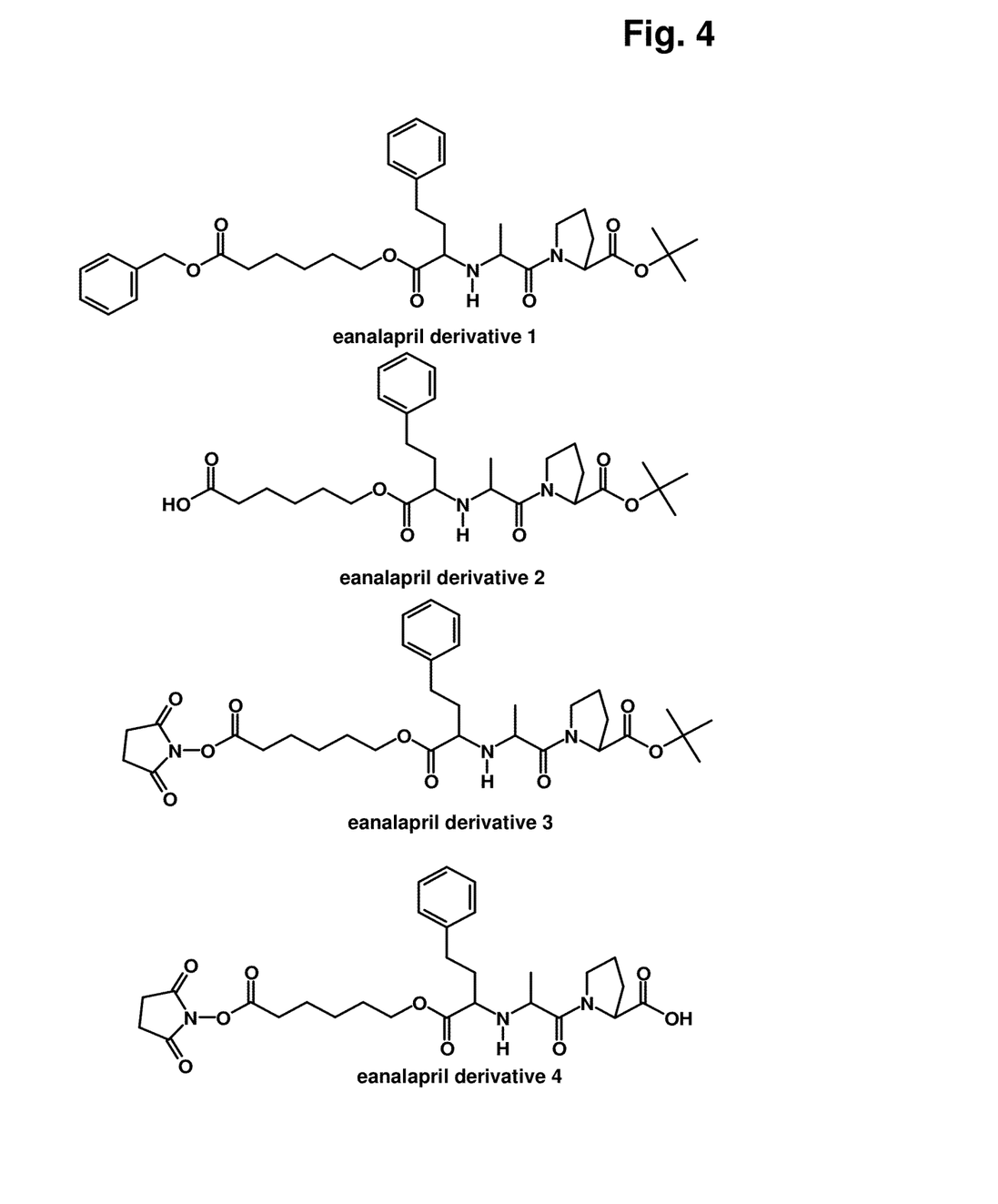
FIG. 4 shows enalapril derivatives corresponding to Example 7.

Enalapril derivative 1 (corresponding to FIG. 4): A solution of enalapril t-butyl ester (2.87 g 7.09 mmol) in THF (20 ml) is added to benzyl hexanoate 6-O—N,N'-diisopropylisourea (2.47 g, 7.09 mmol), 20 mg of DMAP are added, and the mixture is heated under reflux for 7 h, then stirred overnight at 60° C. The reaction solution is cooled in ice, and the solid material is filtered off. The filtrate is evaporated, and the residue is eluted on silica gel with ethyl acetate:hexane 1:2 to 2:1. Clean fractions are evaporated together. Yield 85%.

$^{13}$C and $^1$H-NMR confirm the structure indicated.

Enalapril derivative 2 (corresponding to FIG. 4): Enalapril derivative 1 (400 mg) is dissolved in methanol (50 ml), 10% Pd/C (70 mg) is added, and the mixture is hydrogenated using hydrogen at atmospheric pressure. After 40 min, HPLC shows complete reaction. The catalyst is filtered off, and the solvent is evaporated. The product is used without further purification. $^{13}$C and $^1$H-NMR confirm the structure indicated.

Enalapril derivative 3 (corresponding to FIG. 4): Enalapril derivative 2 (183 mg; 0.35 mmol) is dissolved in acetonitrile (2 ml), and N,N,N',N'-tetramethyl-O—(N-succimidyl)uronium tetrafluoroborate (TSTU) (106 mg; 0.35 mmol) in acetonitrile (2 ml) is added, and N,N-diisopropylethylamine (63 μl; 0.35 mmol) is added, and the mixture is stirred at RT. HPLC shows complete reaction after 5 min. The product is purified by means of preparative HPLC. After lyophilisation, the product is obtained as colourless semi-solid compound. MS (mass spectrometry) shows the exact mass expected.

Enalapril derivative 4 (corresponding to FIG. 4): Enalapril derivative 3 (8 mg) is left to stand at RT dissolved in a mixture of TFA (200 μl) and triisopropylsilane (5 μl). HPLC shows complete reaction after 1 hour. Acetonitrile (1 ml) is added, and the mixture is then evaporated. The residue is dissolved in 1 ml of acetonitrile:water 1:1 and lyophilised. MS shows the exact mass expected.

ε-Polylysine-Enalapril Derivative:

Solution A: 8 mg of enalapril derivative 4 in 100 μl of acetonitrile

Solution B: 100 mg of ε-polylysine in 650 μl of water and 350 μl of acetonitrile 5 μl of N,N-diisopropylethylamine is added to 100 μl of solution B and mixed. 25 μl of solution A is then added and mixed as quickly as possible. After a few minutes, HPLC shows a peak of unreacted ε-polylysine and a new main peak, but no longer a peak for enalapril derivative 4. The newly formed product is isolated by preparative HPLC and characterised by MS as the desired mono-enalapril-ε-polylysine derivative.

DOTA-ε-polylysine-enalapril derivative: An excess of DOTA 2,6-difluorophenyl ester in methanol is added to ε-polylysine-enalapril derivative in water N,N-diisopropylethylamine is added. Purification by preparative HPLC gives the desired compound.

Example 7

Rapamycin Derivative of ε-Polylysine

Rapamycin 42-hemisuccinate: is prepared from rapamycin (LC-Laboratories) succinic anhydride and lipase acrylic resin from *Candida antarictica* (Sigma). (Gu et al. Org. Lett. 2005, 7, 3945-3948)

Rapamycin 42-hemisuccinyl-NHS ester: Rapamycin 42-hemisuccinate (180 mg; 0.177 mmol) is dissolved in acetonitrile (1.5 ml), and N,N,N',N'-tetramethyl-O—(N-succimidyl)uronium tetrafluoroborate (TSTU) (56 mg; 0.186 mmol) in acetonitrile (0.5 ml) is added, and N,N-diisopropylethylamine (36 μl; 0.20 mmol) is added, and the mixture is stirred at RT. HPLC shows complete reaction after 30 min. The product is purified by preparative HPLC. After lyophilisation, the product (125 mg) is obtained as colourless solid compound. MS shows the exact mass expected.

ε-Polylysine-Rapamycin Derivative:

ε-Polylysine (3 ml of 25% aqueous solution; Chisso) is diluted with water (30 ml) and adjusted to pH about 3 using TFA and lyophilised.

Solution A: 30 mg of rapamycin 42-hemisuccinyl-NHS ester in 500 μl of acetonitrile Solution B: 500 mg of ε-polylysine (acidic, see above) is dissolved in 5 ml of water:acetonitrile (2:1) and adjusted to pH 7-7.5 by addition of triethylamine.

Solution A is added to solution B with stirring. A cloudy mixture forms. Addition of acetonitrile (1 ml) causes the formation of a clear solution. HPLC after about 15 min shows complete reaction of the rapamycin 42-hemi-succinyl-NHS ester and formation of a new product besides unreacted ε-polylysine. The newly formed product is isolated by preparative HPLC and characterised by MS as the desired mono-rapamycin-ε-polylysine derivative.

DOTA-ε-polylysine-rapamycin derivative: DOTA 2,6-difluorophenyl ester (20 mg; 40 μmol) in acetonitrile (200 μl is added to the ε-polylysine-rapamycin derivative (10 mg; about 2 μmol) dissolved in water:acetonitrile 2:1 (5000, and the reaction solution is adjusted to pH 7-7.5 by addition of triethylamine and reacted overnight at RT. Purification by preparative HPLC gives, after lyophilisation, the desired compound as colourless solid substance. The number of DOTA groups per molecule is determined by MS. The proportion is between 15 and 18 DOTA units per molecule.

Example 8

Sorafenib Derivative of ε-Polylysine

4-Chloro(2-pyridyl))N-2-hydroxyethylcarboxamide (S-2): Methyl 4-chloropyridine-2-carboxylate hydrochloride (S-1)(2.08 g; 10 mmol) (Bankston et al. Organic Process Research & Development 2002, 6, 777-781) is initially introduced in methanol (5 ml) and cooled in ice. Ethanolamine (3 ml; 50 mmol) in THF (50 ml) added dropwise over the course of 10 min, the mixture is then stirred at 0° for a further 3 h and subsequently at RT overnight. After evaporation, the residue is taken up in ethyl acetate and washed with 5% NaHCO3, the organic solution is dried and evaporated. The product, S-2, (1.84 g 91%) is obtained as pale-yellow solid substance in high purity (HPLC). $^{13}$C NMR (DMSO-$d_6$): δ 42.15, 59.98, 122.30, 126.82, 145.01, 150.43, 152.09, 163.20 p.p.m.

(4-(4-Aminophenoxy)(2-pyridyl))-N-2-hydroxyethylcarboxamide (S-3): K tert-butoxide (3.17 g; 28.24 mmol) is added in portions to a solution of 4-aminophenol (2.96 g; 27.1 mmol) in DMF (45 ml) under argon, and the mixture is then stirred at RT for 1.5 h. A solution of S-2 (5.43 g; 27 mmol) in DMF (10 ml) added, and $K_2CO_3$ (2.0 g) subsequently added. The reaction is heated at 70° in an oil bath for 6 h then cooled, and ethyl acetate (400 ml) and saturated NaCl (400 ml) are added. The aqueous phase is extracted again with ethyl acetate, and the combined organic phases are washed with 4×100 ml of saturated NaCl, dried and evaporated. The dark residue is purified firstly on silica gel with ethyl acetate/hexane (3:1)-ethyl acetate/methanol (10:1). Fractions containing product are evaporated together and then eluted on alumina with ethyl acetate/hexane (3:1)-ethyl acetate/methanol (10:1). The product as pale-yellow solid substance (3.20 g; 43%) in high purity (HPLC) MS: M+Na=296.100; calculated for $C_{14}H_{15}N_3NaO_3$=296.1011.

N-(4-Chloro-3-(trifluoromethyl)phenyl)-((4-(2-(N-hydroxyethyl-carbamoyl)(4-pyridyloxy))phenyl)amino)carboxamide (S-4): A solution of S-3 (1.50 g; 5.49 mmol) in dichloromethane (20 ml) is cooled in ice, and a solution of 4-chloro-3-trifluoromethylphenyl isocyanate (1.26 g; 5.70 mmol) in dichloromethane (20 ml) is added. After 1 h, the precipitated solid substance is filtered off and rinsed with dichloromethane and dried. The product (S-4) (2.34 g; 4.73 mmol; 86%) is obtained as white solid substance. MS: M+H=495.1037 calculated for $C_{22}H_{19}ClF_3N_4O_4$: 495.1047.

Sorafenib derivative S-5: S-4 (2.30 g; 4.65 mmol) is dissolved in pyridine (15 ml), and a solution of succinic anhydride (581 mg; 5.81 mmol) in pyridine (5 ml) is added, N,N-dimethylaminopyridine (284 mg; 2.33 mmol) is added, and the mixture is stirred overnight at RT. The reaction mixture applied to a column containing about 20 ml of pyridinium-Dowex in pyridine:methanol:water (8:1:1) and eluted with the same mixture. The eluate is evaporated, the residue is evaporated a number of times with toluene finally with acetonitrile. The product (S-5) is obtained as white foam (2.65 g; 4.45 mmol; 95%) MS: M+H=595.1115; calculated for $C_{26}H_{23}ClF_3N_4O_7$: 595.1207.

Sorafenib derivative S-6: S-5 (180 mg; 0.30 mmol) was dissolved in acetonitrile (3 ml), and a solution of N,N,N',N'-tetramethyl-O—(N-succinimidyl)uronium tetrafluoroborate (TSTU) (99 mg; 0.32 mmol) in acetonitrile (3 ml) was added, and N,N-diisopropylethylamine (67 µl; 0.37 mmol) was added. HPLC shows complete reaction after 10 min. 0.1% TFA in water (2 ml) is added, and the mixture is purified preparatively HLPC. S-6 is obtained as "off-white" solid substance (163 mg; 0.24 mmol; 78%). MS: M+H=692.1368; calculated for $C_{30}H_{25}ClF_3N_5O_9$: 692.1371.

ε-Polylysine-Sorafenib Derivative:

ε-Polylysine (3 ml of 25% aqueous solution; Chisso) is diluted with water (30 ml) and adjusted to pH about 3 using TFA and lyophilised.

Solution A: 17 mg of sorafenib derivative S-6 in 500 µl of acetonitrile

Solution B: 500 mg of ε-polylysine (acidic, see above) is dissolved in 5 ml of water:acetonitrile (2:1) and adjusted to pH7-7.5 by addition of triethylamine.

Solution A is added to solution B with stirring. A cloudy solution forms. Addition of acetonitrile (1 ml) causes the formation of a clear solution. HPLC after about 15 min shows complete reaction of the sorafenib derivative S-6 formation of a new product besides unreacted ε-polylysine. The newly formed product (71 mg) is isolated by preparative HPLC and characterised by MS as the desired mono-sorafenib-ε-polylysine derivative.

DOTA-ε-polylysine-sorafenib derivative: DOTA 2,6-fluorophenyl ester (197 mg; 360 µmol) in acetonitrile (1.5 ml) is added to ε-polylysine-sorafenib derivative (71 mg; about 15 µmol) dissolved in water:acetonitrile 2:1 (1.5 ml), and the reaction solution is adjusted to pH 7-7.5 by addition of triethylamine and reacted overnight at RT. Purification by preparative HPLC gives, after lyophilisation, the desired compound as colourless solid substance (90 mg). The number of DOTA groups per molecule is determined by MS as 16-20.

2. Use Examples

1. Organ Distribution Study

In order to determine the pharmacokinetics, ε-polylysine-DOTA is labelled with the radioactive nuclide $^{111}$In in accordance with Synthesis Example 2/3 and NMRI mice are injected in groups of three animals each via the tail vein. The amount used is about 5 µg of ε-polylysine-DOTA per animal, the dose is about 1 MBq per animal.

The animals are subsequently dissected, and the isolated organs (blood, heart, lung, spleen, liver, kidney, muscle, brain) are investigated with respect to their radioactivity in a gamma counter. The amount of radioactivity in the corresponding organ represents directly the amount of ε-polylysine-DOTA taken up. The animals are killed after various times. This is carried out, like the entire performance of the experiment, in accordance with the ethical principles for scientific performance of animal experiments. Surprisingly, it is observed in the measurements that over 150 per cent of the injected dose per gram of kidney tissue accumulates in the kidneys of the experimental animals only 10 minutes after injection of the $^{111}$In-loaded ε-polylysine-DOTA. A small proportion is excreted via the urine.

The graphical representation of the accumulation in the various organs investigated is shown in FIG. 2. The Y axis represents the specific accumulation in the particular organs—indicated as per cent of the injected dose per gram of tissue. P1 to P3 represent the results for conjugates with various degree of loading: P1: about 10% of the lysine monomers carry a DOTA, P2: about 30% of the lysine monomers carry a DOTA and P3: about 50% of the lysine monomers carry a DOTA.

2. PET Measurement

For PET measurements, labelling is carried out with 68-gallium, in accordance with Synthesis Example 4, and the kidney accumulation is investigated dynamically in a small-animal PET scanner (Siemens). It is found here that the compound (ε-L-polylysine-DOTA, loaded with $^{68}$Ga) achieves an extraordinarily good organ to background ratio and accumulates virtually exclusively in the kidney. Typical values here are a 10-fold accumulation in the kidney in relation to the remainder of the body.

3. Comparative Experiments

The uptake of $^{99m}$Tc-MAG3 and of $^{99m}$Tc-DMSA are compared with the uptake of (ε-L-polylysine-DOTA, loaded with $^{111}$In) in the rat and mouse model in planar scintigraphs. Both known tracers exhibit a worse kidney to background ratio than the substance according to the invention.

3. Conjugation of Various Compounds Carrying Carboxyl Groups

In order to investigate the effect of various compounds carrying carboxyl groups on the accumulation in the kidney, ε-polylysine is conjugated with a DOTA unit in order to facilitate labelling with radionuclides for animal experiments. In addition to the one DOTA unit, a plurality of units of another compound carrying carboxyl groups or of a compound which carries no carboxyl groups are conjugated on. Organ distribution studies of these conjugates show that conjugates with DO-3AM (1,4,7,10-tetraazacyclo-dodecane-N, -N', -N", -triamide, N'"-monoacetic acid, Macrocyclics), which contains no carboxyl groups after conjugation, exhibit an accumulation in the kidney which do not exceed the accumulation already achieved with a DOTA group, while the conjugates with citric acid exhibit excellent accumulation and the conjugates with succinic acid exhibit good accumulation in the kidney.

Synthesis of an ε-polylysine with only one DOTA unit per molecule (Ref. 1): ε-Polylysine (780 mg) is dissolved in water:methanol 1:1, and DOTA 2,6-difluorophenyl ester (103 mg) in methanol is added, diisopropylethylamine (100 μl) is added, and the mixture is stirred overnight at RT. The product is purified by HPLC and lyophilised. MS shows a mixture of ε-polylysine and ε-polylysine-1×DOTA in the ratio about 2:1. This compound, Ref. 1, is used for the preparation of all following derivatives.

DO-3AM-acetic acid derivative of Ref. 1: DO-3AM-acetic acid (42 mg) and TSTU (31 mg) are dissolved in DMF (2 ml), and diisopropylethylamine (18 μl) is added. After 1 min, this solution is added to Ref. 1 (16 mg) in water:dioxane 1:1 (4000 and left to react at RT overnight. After dilution with water, the product is purified HPLC and lyophilised.

Citric acid derivative of Ref. 1: Citric anhydride is prepared from citric acid (2 mmol) and dicyclohexylcarbodiimide (1 mmol) in THF (5 ml). After 30 min, the dicyclohexylurea formed is filtered off and rinsed with THF. The filtrate is evaporated and used further directly. Citric anhydride (80 mg) in pyridine (200 μl) is added to a solution of Ref. 1 (38 mg) and dimethylaminopyridine (5 mg) in pyridine:water 1:1 (2000, and the mixture is stirred at RT overnight. After dilution with water, the product is purified HPLC and lyophilised. The number of citric acid units per molecule of ε-polylysine-1×DOTA can be determined by MS as 4-8.

Succinic acid derivative of Ref. 1: Succinic anhydride (100 mg) in pyridine:dioxane 1:1 (2000 μl) is added to a solution of Ref. 1 (38 mg) and dimethylaminopyridine (5 mg) in pyridine:water 1:1 (10000, and the mixture is stirred at RT overnight. After dilution with water, the product is purified by HPLC and lyophilised.

The invention claimed is:

1. A conjugate comprising at least one compound carrying carboxyl groups and an oligomer which consists of 10 to 1000 peptidically linked monomer units and which is either built up from more than 50% (based on the total number of monomer units) of ε-lysine monomer units or comprises at least 10 successive monomer units which are built up from at least 70% (based on the number of such successive monomer units) of ε-lysine monomer units,
    wherein the conjugate contains from 3 to 6 compounds carrying carboxyl groups per 10 monomer units,
    wherein, in the oligomer, said ε-lysine monomer units are bonded via the ε-amino group of their side chain, such that the oligomer is unbranched,
    wherein, in the compound carrying carboxyl groups, the proportion of carboxyl groups by molecular weight is greater than 30% and
    wherein at least one compound carrying carboxyl groups which is conjugated to the oligomer contains two or more free carboxyl groups.

2. The conjugate of claim 1, wherein, in addition, at least one active compound is covalently bonded to the conjugate.

3. The conjugate of claim 1, wherein the oligomer has a chain length of 10 to 50 monomer units.

4. The conjugate of claim 1, wherein the oligomer consists only of ε-lysine monomer units.

5. The conjugate of claim 1, wherein the oligomer consists of ε-polylysine.

6. The conjugate of claim 1, wherein at least one compound carrying carboxyl groups is bonded, directly or via a spacer, to the amino group of an ε-lysine monomer unit.

7. The conjugate of claim 1, wherein at least one compound carrying carboxyl groups is a complexing agent.

8. A process for the preparation of a conjugate of claim 1 which comprises at least the following process steps:
    a) providing an oligomer which consists of peptidically linked monomer units and which is either built up from more than 50% (based on the total number of monomer units) of ε-lysine monomer units or comprises at least 10 successive monomer units which are built up from at least 70% (based on the number of such successive monomer units) of ε-lysine monomer units, such that the oligomer is unbranched, and
    b) conjugating with the oligomer at least one compound carrying two or more free carboxyl groups to the oligomer from step a), wherein, optionally, at least one active compound is covalently bonded to the conjugate such that the conjugate contains from 3 to 6 compounds carrying carboxyl groups per 10 monomer units.

9. A medicament composition comprising a conjugate of claim 1.

10. A method for targeting of the kidney with a drug comprising administering the drug together with a conjugate of claim 1.

11. A macromolecule conjugate composed of at least two conjugates according to claim 1 which are covalently bonded to a macromolecule.

12. A therapeutic or image-enhancing composition, comprising a conjugate corresponding to claim 1.

13. A kit for the preparation of a medicament comprising a conjugate corresponding to claim 1.

14. A kit according to claim 13, for the preparation of a therapeutic or image-enhancing composition.

15. The conjugate of claim 2, wherein the active compound is selected from the group consisting of: immunosuppressants, cytostatics, protein kinase inhibitors, immunotherapeutic agents, antiphlogistics, antibiotics, cephalosporins, β-lactamase inhibitors, carbapenems, monobactams, tetracyclines, macrolide antibiotics, glycopeptide antibiotics, enediynes, virostatics, antihypertensives, sartans, renin inhibitors, beta blockers, uricosurics, and diuretics.

16. The conjugate of claim 2, wherein the active compound is selected from the group consisting of: azathioprine, mycophenolate-mofetil, ciclosporin, tacrolimus, sirolimus, fingolimod, triptolide, bleomycin, dactinomycin, mitomycin, daunorubicin, doxorubicin, epirubicin, idarubicin, mitoxantron, amsacrine, doxofluridine, cisplatin, carboplatin, oxaliplatin, satraplatin, camptothecin, toptecan, irinotecan, etoposide, teniposide, cyclophosphamide, trofosfamide, melphalan, chlorambucil, estramustine, busulfan, chlorambucil, chlormethine, treosulfan, carmustine, lomustine, nimustine, procarbazine, streptozocine, dacarbazine, ifosfamide, temozolomide, thiotepa, vinorelbine, vincristine, vinblastine, vindesine, paclitaxel, docetaxel, methotrexate, pemetrexed, raltitrexed, fluorouracil, capecitabine, cytosinarabinoside, gemcitabine, tioguanine, pentostatin, mercaptopurine, fludarabine, caldribine, hydroxycarbamide, mitotane, azacitidine, cytarabine, nelarabine, bortezomib, anagrelide, imatinib, erlotinib, sunitinib, sorafenib, dasatinib, lapatinib or nilotinib, cetuximab, alemtuzumab, bevacizumab, naproxen, ibuprofen, indometacin, prednisolone, prednisone, hydrocortisone, budesonide, benzylpenicillin, methicillin, amoxicillin, cefuroxim, cefotaxim, cefadroxil, cefixim, clavulanic acid, sulbactam, tazobactam, imipenem, meropenem, aztreonam, tetracycline, chlortetracycline, oxytetracycline, doxycycline, minocycline, tigecycline, erythromycin A, vancomycin, calicheamicin, aciclovir, valaciclovir, ganciclovir, valganciclovir, penciclovir, famciclovir, brivudine, cidofovir, foscarnet, idoxuridine, tromantadine, benazepril, captopril, cilazapril, enalapril, fosinopril, lisinopril, perindopril, quinapril, ramipril, trandolapril, zofenopril, losartan, balsartan, irbesartan, candesartan, eprosartan, olmesartan, telmisartan, aliskiren, proproanolol, pindolol, sotalol, bopindolol, atenolol, bisorpolol, celiprolol, esmolol, metoprolol, nebivolol, oxprenolol, carvedilol, labetalol, probenecid, benzbromarone, acetazolamide, furosemide, torasemide, bumetanide, piretanide, azosemide, etacrynic acid, etozoline, hydrochlorothiazide, benzthiazide, chlorothiazide, chlorthalidone, indapamide, mefruside, metolazone, clopamide, xipamide, hydroflumethiazide, methyclothiazide, polythiazide, amiloride, triameterene, spironolactone, canrenone, eplerenone and spironolactone.

17. The conjugate of claim 1, wherein the compound carrying carboxyl groups is 1,4,7,10-tetraazacyclododecane-N, -N', -N", -N'''-tetraacetic acid or diethylenetriaminepentaacetic acid.

\* \* \* \* \*